US005731185A

United States Patent [19]

Meda et al.

[11] Patent Number: 5,731,185

[45] Date of Patent: Mar. 24, 1998

[54] ISOLATED DNA ENCODING THE HPHI RESTRICTION ENDONUCLEASE AND RELATED METHODS FOR PRODUCING THE SAME

[75] Inventors: Marta M. Meda, Beverly; Julie Forney Menin, Newburyport, both of Mass.

[73] Assignee: New England Biolabs, Inc., Beverly, Mass.

[21] Appl. No.: 505,691

[22] Filed: Jul. 21, 1995

[51] Int. Cl.$^6$ .............................. C12N 9/22; C12N 15/55
[52] U.S. Cl. .................. 435/194; 435/252.3; 435/320.1; 536/23.1
[58] Field of Search .................... 435/199, 320.1, 435/252.3; 536/23.2

[56] References Cited

U.S. PATENT DOCUMENTS

| | | | |
|---|---|---|---|
| 4,983,522 | 1/1991 | Barsomian et al. | 435/172.3 |
| 4,999,293 | 3/1991 | Barsomian et al. | 435/172.3 |
| 5,015,581 | 5/1991 | Benner et al. | 435/172.3 |
| 5,179,015 | 1/1993 | Wilson et al. | 435/172.3 |
| 5,196,332 | 3/1993 | Wilson | 435/199 |
| 5,200,333 | 4/1993 | Wilson | 435/172.3 |
| 5,215,906 | 6/1993 | Wilson | 435/199 |
| 5,298,404 | 3/1994 | Benner et al. | 435/199 |

OTHER PUBLICATIONS

Lubys, A., et al. (1996) Nucl. Acids Res. 24(14), 2760–2766.
Miller, Experiments In Molecular Genetics; Cold Spring Harbor Laboratories Cold Spring Harbor, NY (1972) pp. 82–85.
Demerec, et al., Genetics, 54:61–76 (1966).
Wang, et al., Cold Spring Harbor Symposium, 47:85–91 (1983).
Simons, Gene, 53:85–96 (1987).
Maniatis, Molecular Cloning, Cold Spring Harbor, pp. 366–367 (1982).
Lunnen, et al., Gene, 74:25–32 (1988).
Raleigh and Wilson, Proc. Natl. Acad. Sci., USA, 83:9070–9074 (1986).
Heitman and Model, J. Bact., 196:3243–3250 (1987).
Raleigh, et al., Genetics, 122:279–296 (1989).
Waite–Rees, et al., J. Bacteriology, 173:5207–5219 (1991).
Raleigh, et al., Meth. Enzymology, 152:130–141 (1987).
Southern, J. Mol. Biol., 98:503 (1975).
Kong, et al., J. Biol. Chem. 268:1965–1975 (1993).
Studier, et al., Methods Enzymology, 185:60–89 (1990).
Yanisch–Perron, et al., Gene, 33:103–119 (1985).
Mi and Roberts, Nucleic Acids Res., 20:4811–4816 (1992).
Kosykh, et al., Molec. Gen. Genet., 178:717–719 (1980).
Mann, et al., Gene, 3:97–112 (1978).
Walder, et al., Proc. Nat. Acad. Sci., 78:1503–1507 (1981).
Bougueleret, et al., Nucl. Acid Res. 12:3659–3676 (1984).
Gingeras and Brooks, Proc. Natl. Acad. Sci. USA 80:402–406 (1983).
Theriault and Roy, Gene, 19:355–359 (1982).
Blumenthal, et al., J. Bacteriol., 164:501–509 (1985).
Kiss, et al., Nucl. Acid Res., 13:6403–6421 (1985).
Szomolanyi, et al., Gene, 10:219–225 (1980).
Janulaitis, et al., Gene, 20:197–204 (1982).
Kiss and Baldauf, Gene, 21:111–119 (1983).
Walder, et al., J. Biol. Chem., 258:1235–1241 (1983).
Piekarowicz, et al., Nucl. Acids Res., 19:1831–1835 (1991).
Piekarowicz, et al., J. Bacteriology, 173:150–155 (1991).
Fomenkov, et al., Nucl. Acids Res., 22:2399–2403 (1994).

*Primary Examiner*—Charles L. Patterson, Jr.
*Attorney, Agent, or Firm*—Gregory D. Williams

[57] ABSTRACT

The present invention is directed to a method for cloning and producing the HphI restriction endonuclease by 1) linking up the restriction gene to transcription elements that can be processed in *E. coli* and 2) expressing DNA modification enzymes in the host that protect against HphI digestion.

6 Claims, 7 Drawing Sheets

FIG. I

HphCM5-3
FIG. 2
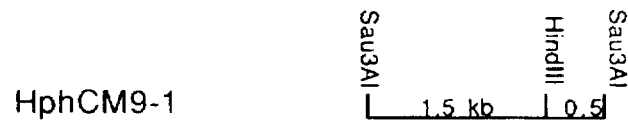
HphCM9-1
*Hph*I Endonuclease Protein Sequence at N-Terminal
```
ATG CAR ATH TAY GAR ACN TAY TGG GAR ATH ACN AAY GAR TAY   42
Met Gln Ile Try Glu Thr Tyr Trp Glu Ile Thr Asn Glu Tyr
1                5                       10
GGN TAY AAY ACN GCN CGN TTY GTN GAR ACN AGR                75
Gly Tyr Asn Thr Ala Arg Phe Val Glu Thr
15              20
```
Underlining denotes degenerate oligonucleotide
R = A or G
N = A, C, G, or T
Y = C or T
H = A, C, or T
FIG. 3
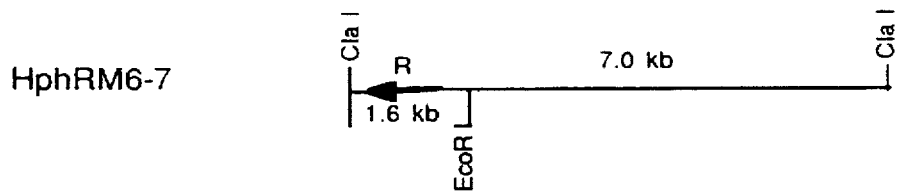
HphRM6-7
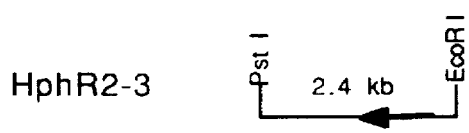
HphR2-3
FIG. 4

Amplification #1:
pUC19-HphR2-3
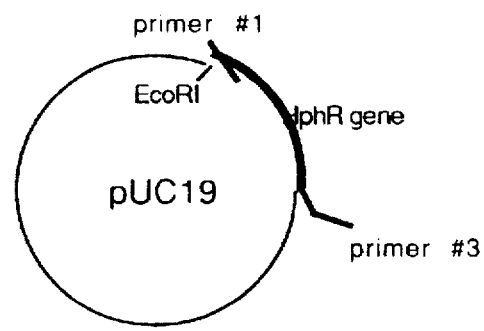
HphRgene #1:
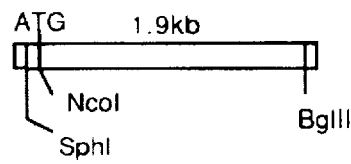
Amplification #2:
pUC19-HphR2-3
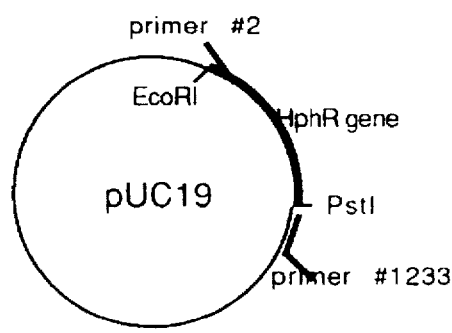
HphRgene #2:
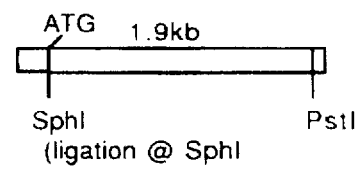
(ligation @ SphI
to pUC19 couples
gene synthesis to lac Z synthesis)
FIG. 5 rrnb = ribosome transcription terminators

M1 = HphI 5- methyl Cytosine Methylase
M2 = HphI 6- methyl Adenine Methylase
R = HphI Endonuclease
aa = amino acids

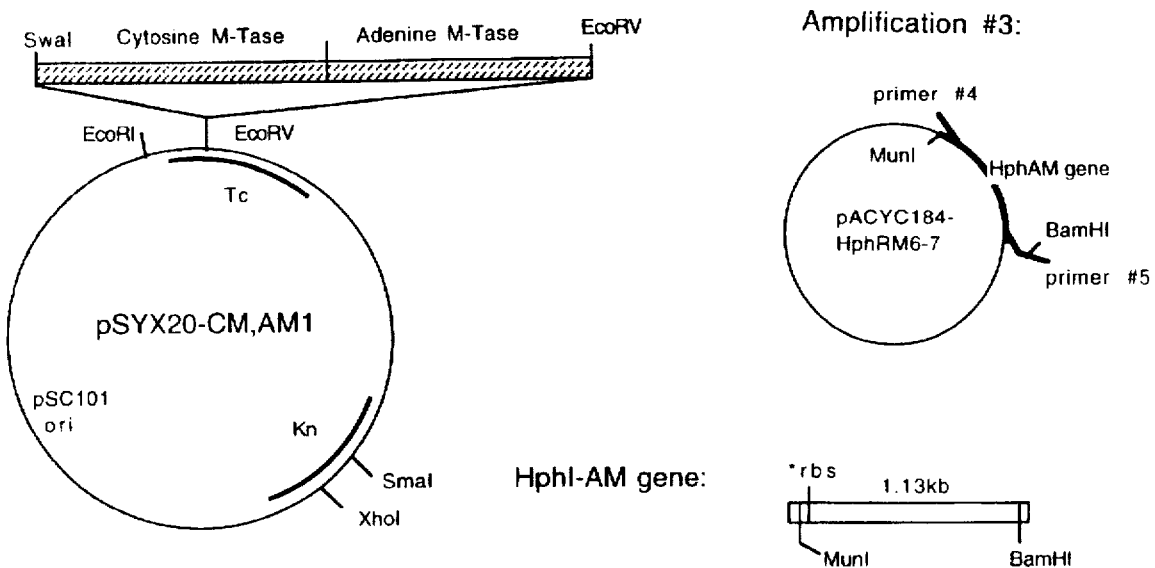
FIG. 8d
FIG. 9
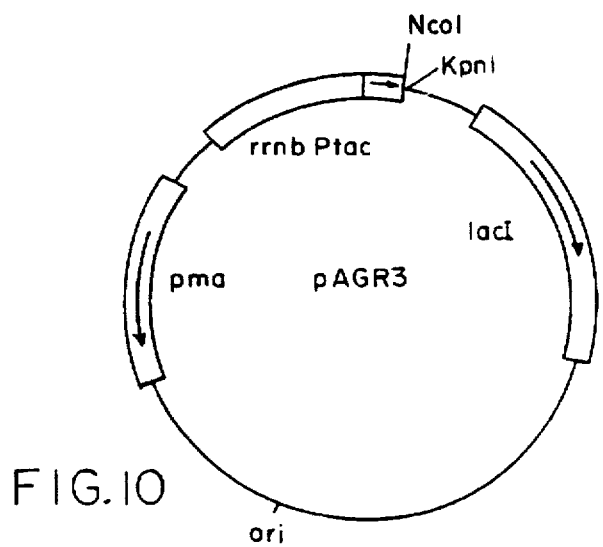
FIG. 10

ISOLATED DNA ENCODING THE HPHI RESTRICTION ENDONUCLEASE AND RELATED METHODS FOR PRODUCING THE SAME

BACKGROUND OF THE INVENTION

The present invention relates to recombinant DNA which encodes the HphI restriction endonuclease and modification methylases, and the production of these enzymes from the recombinant DNA.

Restriction endonucleases are a class of enzymes that occur naturally in bacteria. When they are purified away from other contaminating bacterial components, restriction endonucleases can be used in the laboratory to cut DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. More than one hundred different restriction endonucleases have been identified among the many hundreds of bacterial species that have been examined to date.

Bacteria tend to possess only a small number of restriction endonucleases per species. The endonucleases typically are named according to the bacteria from which they are derived. Thus, the species *Neisseria lactamica* for example, synthesizes four different restriction endonucleases, named NlaI, NlaII, NlaIII and NlaIV. These enzymes recognize and cleave the sequences GGCC, GATC, CATG and GGNNCC respectively. *Escherichia coli* RY13, on the other hand, synthesizes only one enzyme, EcoRI, which recognizes the sequence GAATTC.

While not wishing to be bound by theory, it is thought that in nature restriction endonucleases play a protective role in the welfare of the bacterial cell. They enable bacteria to resist infection by foreign DNA molecules like viruses and plasmids that would otherwise destroy or parasitize them. They impart resistance by scanning the lengths of the infecting DNA molecule and cleaving them each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and provide the means by which bacteria are able to protect their own DNA and distinguish it from foreign, infecting DNA. Modification methylases recognize and bind to the same nucleotide recognition sequence as the corresponding restriction endonuclease, but instead of cleaving the DNA, they chemically modify one or other of the nucleotides within the sequence by the addition of a methyl group. Following methylation, the recognition sequence is no longer bound or cleaved by the restriction endonuclease. The DNA of a bacterial cell is fully modified by virtue of the activity of its modification methylase, and is therefore insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins that they encode in greater quantities than are obtainable by conventional purification techniques. The standard approach to isolating clones of interest (restriction endonuclease genes) is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Molec. Gen. Genet* 178:717–719, (1980); HhaII: Mann et al., *Gene* 3:97–112, (1978); PstI: Walder et al., *Proc. Nat. Acad. Sci.* 78:1503–1507, (1981), the disclosures of which are hereby incorporated by reference herein). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acid. Res.* 12:3659–3676, (1984); PaeR7: Gingeras and Brooks, *Proc. Natl. Acad. Sci. USA* 80:402–406, (1983); Theriault and Roy, *Gene* 19:355–359 (1982); PvuII: Blumenthal et al., *J. Bacteriol.* 164:501–509, (1985), the disclosures of which are hereby incorporated by reference herein).

A third approach, which is being used to clone a growing number of systems, involves selection for an active methylase gene (See e.g., U.S. Pat. No. 5,200,333 and BsuRI: Kiss et al., *Nucl. Acid. Res.* 13:6403–6421, (1985), the disclosures of which are hereby incorporated by reference herein). Since restriction and modification genes are often closely linked, both genes can often be cloned simultaneously. This selection does not always yield a complete restriction system however, but instead yields only the methylase gene (BspRI: Szomolanyi et al., *Gene* 10:21 9–225, (1980); BcnI: Janulaitis et al, *Gene* 20:197–204 (1982); BsuRI: Kiss and Baldauf, *Gene* 21:111–119, (1983); and MspI: Walder et al., *J. Biol. Chem.* 258:1235–1241, (1983), the disclosures of which are hereby incorporated by reference herein).

Another method for cloning methylase and endonuclease genes is based on a colorimetric assay for DNA damage. When screening for a methylase, the plasmid library is transformed into the host *E. coli* strain such as AP1–200. The expression of a methylase will induce the SOS response in an *E. coli* strain which is McrA+, McrBC+, or Mrr+. The AP1-200 strain is temperature sensitive for the Mcr and Mrr systems and includes a lac-Z gene fused to the damage inducible dinD locus of *E. coli*. The detection of recombinant plasmids encoding a methylase or endonuclease gene is based on induction at the restictive temperature of the lacZ gene. Transformants encoding methylase genes are detected on LB agar plates containing X-gal as blue colonies. (Piekarowicz, et. al., *Nucleic Acids Res.* 19:1831–1835, (1991) and Piekarowicz, et. al. *J. Bacteriology* 173:150–155 (1991), the disclosures of which are hereby incorporated by reference herein). Likewise, the *E. coli* strain ER1992 contains a dinD1-Lac Z fusion but is lacking the methylation dependent restriction systems McrA, McrBC and Mrr. In this system (called the "endo-blue" method), the endonuclease gene can be detected in the absence of it's cognate methylase when the endonuclease damages the host cell DNA, inducing the SOS response. The SOS-induced cells form deep blue colonies on LB agar plates supplemented with X-gal (Xu et. al. *Nucleic Acids Res.* 22:2399–2403 (1994), the disclosure of which is hereby incorporated by reference herein).

Sometimes the straight-forward methylase selection method fails to yield a methylase (and/or endonuclease) clone due to various obstacles. See, e.g., Lunnen, et al., *Gene*, 74(1):25–32 (1988), the reference of which is hereby incorporated by reference herein. One potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease.

Another obstacle to cloning restriction-modification systems lies in the discovery that some strains of *E. coli* react adversely to cytosine or adenine modification; they possess systems that destroy DNA containing methylated cytosine (Raleigh and Wilson, *Proc. Natl. Acad. Sci., USA* 83:9070–9074, (1986), the disclosure of which is hereby incorporated by reference herein) or methylated adenine (Heitman and Model, *J. Bact.* 196:3243–3250, (1987); Raleigh, Trimarchi, and Revel, *Genetics*, 122:279–296, (1989) Waite-Rees, et al., *J. Bacteriology,* 173:5207–5219 (1991), the disclosures of which are hereby incorporated by reference herein). Cytosine-specific or adenine-specific methylase genes cannot be cloned easily into these strains, either on their own, or together with their corresponding endonuclease genes. To avoid this problem it is necessary to use mutant strains of *E. coli* (McrA⁻ and McrB⁻ or Mrr⁻) in which these systems are defective.

A third potential difficulty is that some restriction endonuclease and methylase genes may not express in *E. coli* due to differences in the transcription machinery of the source organism and *E. coli*, such as differences in promotor and ribosome binding sites. The methylase selection technique requires that the methylase express well enough in *E. coli* to fully protect at least some of the plasmids carrying the gene.

For example, several restriction-modification systems have been identified from the Haemophilus species of bacteria. Of the known systems, the following restriction enzymes from Haemophilus species have been cloned and characterized by New England Biolabs, Inc. (Beverly, Mass.): HaeII (U.S. Pat. No. 5,196,332, the disclosure of which is hereby incorporated by reference herein), HaeIII (U.S. Pat. No. 5,179,015, the disclosure of which is hereby incorporated by reference herein), HgaI, HhaI (U.S. Pat. No. 4,999,293, the disclosure of which is hereby incorporated by reference herein), HincII (U.S. Pat. No. 5,015,581, the disclosure of which is hereby incorporated by reference herein), HindIII (U.S. Pat. No. 5,180,673, the disclosure of which is hereby incorporated by reference herein), HinfI (U.S. Pat. No. 5,215,906, the disclosure of which is hereby incorporated by reference herein), HinPI (U.S. Pat. No. 4,983,522, the disclosure of which is hereby incorporated by reference herein), and HpaI (U.S. Pat. No. 5,298,404, the disclosure of which is hereby incorporated by reference herein). For each of these Haemophilus-source enzymes, expression of the restriction gene in *E. coli* was achieved by isolating the gene on a restriction fragment, ligating the fragment into an *E. coli*-compatible plasmid and transforming an *E. coli* strain of bacteria with the recombinant plasmid.

As discussed below, for HphI, another endonuclease which is purified from a Haemophilus strain, it was anticipated that the method for expressing the gene would be similar to the previously cited work; however, this was not the case. When the cloning protocol used for HaeII and HaeIII was implemented for cloning HphI, there was no detectable endonuclease activity. In fact, the only verification that the restriction gene had successfully been cloned from two libraries came from subsequent hybridization experiments. Ultimately, the expression of HphI required identifying the location of the restriction gene, determining the DNA sequence of the beginning of the gene and linking it up to new transcription elements.

Because purified restriction endonucleases, such as HphI, are useful tools for characterizing and rearranging DNA in the laboratory, there is a commercial incentive to obtain a strain of bacteria through recombinant DNA techniques which synthesizes this enzyme in abundance. Such a strain would be useful because they would simplify the task of purification as well as providing the means for production in commercially useful amounts.

SUMMARY OF THE INVENTION

The present invention relates to recombinant DNA encoding the genes for the HphI restriction endonuclease and modification methylase obtainable from *Haemophilus parahaemolyticus* (ATCC No. 49700) as well as related methods for the production of these enzymes from the recombinant DNA. The known methods for cloning restriction endonuclease genes were not successful in cloning HphI restriction endonuclease and modification methylase genes. Numerous attempts were made with the very successful method of selecting for an active methylase gene as well as the phage selection method. It is now known that these methods do not work because the endonuclease gene is not expressed in detectable amounts when using the above methods. Therefore a novel approach was required in order to clone the HphI endonuclease and methylase genes. The new method involves purifying the HphI restriction endonuclease to homogeneity and determining the amino acid sequence of the N-terminal end. The amino acid sequence is used to make PCR primers to amplify a portion of the endonuclease directly from the genome, which then serves as a probe to identify clones containing the entire gene. Moreover, in order to express HphI in *E. coli* it was necessary to introduce exogenous transcription elements upstream of the HphI endonuclease gene.

This invention also relates to a transformed host which expresses the restriction endonuclease HphI, an enzyme which recognizes the DNA sequence

GGTGA(N)₈▼
CCACT(N)₇▲

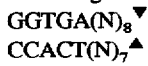

and cleaves as indicated by the arrows. HphI restriction endonuclease produced in accordance with the present invention is substantailly pure and free of the contaminants normally found in restriction endonuclease preparations made by conventional techniques.

BRIEF DESCRIPTION OF THE FIGURES

FIG. 2 illustrates the restriction enzyme maps of the two HphI methylase clones recovered in methylase selection of initial libraries.

FIG. 3 is the DNA sequence (SEQ ID NO:1) of the degenerate oligonucleotide synthesized for DNA amplication and the amino acid sequence (SEQ ID NO:2) of the N-terminus of the HphI endonuclease.

FIG. 4 illustrates the restriction enzyme maps of two clones containing the HphI endonuclease gene.

FIG. 5 is a diagram of the DNA amplification components and the products of those amplifications.

FIG. 8d is the DNA construct used in pre-modification of cells for HphI gene expression using clone pSYX20-CM, AM1.

FIG. 9 is a diagram of the DNA amplification of the adenine methylase gene.

FIG. 10 is a diagram of plasmid pAGR3.

DETAILED DESCRIPTION OF THE INVENTION

The present invention relates to the recombinant DNA encoding for the HphI restriction endonuclease as well as to the enzyme produced from such recombinant DNA. At the onset of the cloning project, it was assumed that all Haemophilus restriction-modification systems readily express in *E. coli* host strains. The cloning results and subsequent mapping and characterization of the clones described in Example I reveal the previously unknown direct pathway for cloning and expressing the HphI restriction-modification system.

Figure 1:
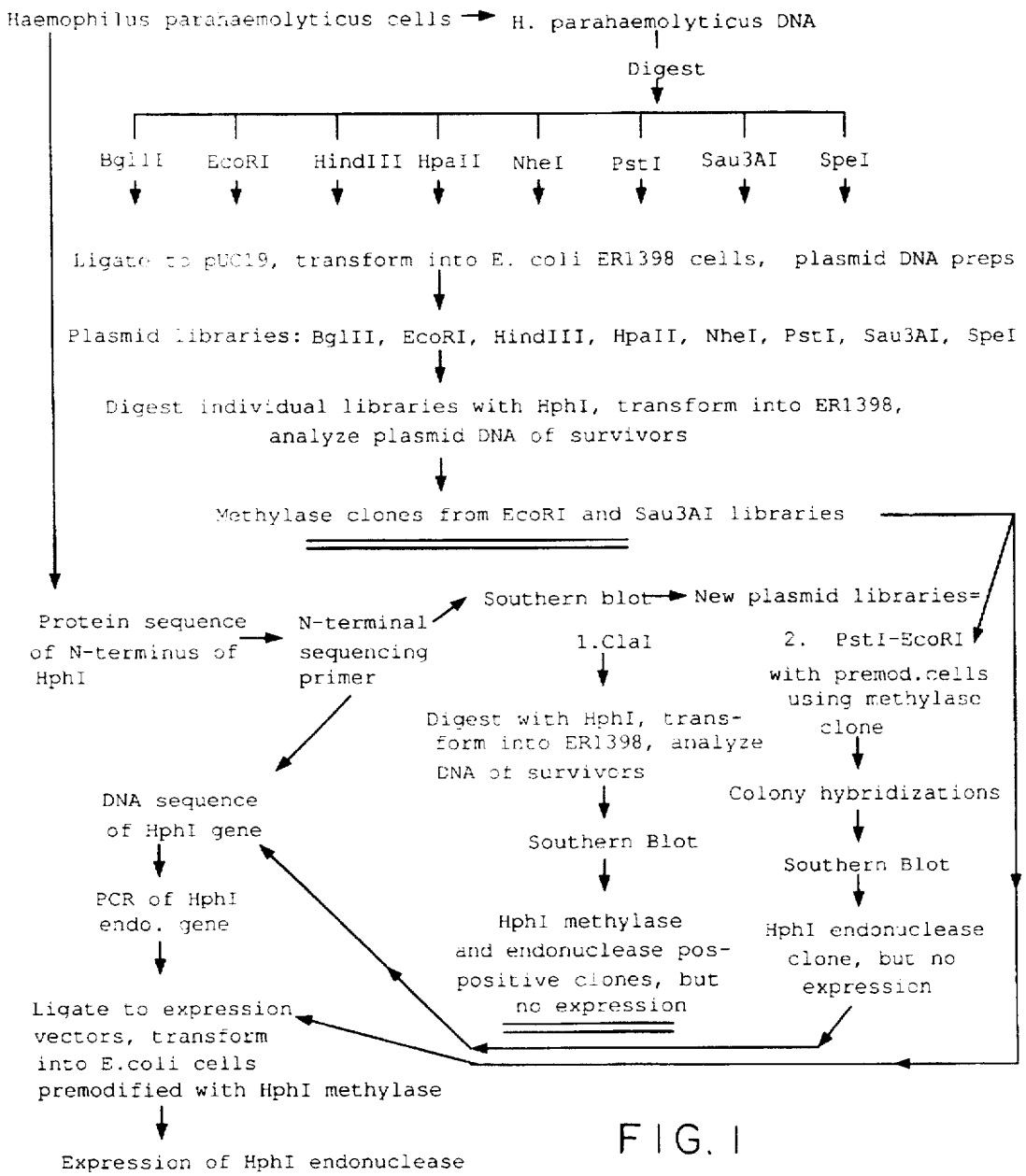
FIG. 1 is the step-wise scheme for cloning and expressing HphI endonuclease.

The method described herein by which the HphI restriction gene and methylase genes are cloned and expressed is illustrated in FIG. 1 and includes the following steps:

1. *Haemophilus parahaemolyticus* (ATCC No. 49700) is grown in Tryptone-yeast extract broth. The cells are concentrated, lysed and genomic DNA is purified as described in Example 1.

2. Plasmid DNA libraries are made using *H. parahaemolyticus* chromosomal DNA digested with various restriction enzymes, including EcoRI, and ligating the digested DNA's to a cloning vector, such as pUC19 (ATCC No. 37254). The resulting recombinant plasmids are used to transform an appropriate host, such as *E coli* ER1398 (Raleigh, et al., *Meth. Enzymology*, 152:130–141 (1987), the disclosure of which is hereby incorporated by reference herein). Following transformations, the cells are grown in selective media and the plasmid DNA is purified using a DNA purification procedure described in Example 1.

3. The plasmid libraries are methylase selected by digesting the DNAs with HphI which destroys non-HphI methylated plasmids. This enriches the plasmid pool with plasmids carrying and expressing an HphI methylase. Transformations are made with the methylase-selected plasmid pool and individual clones are selected and analyzed for methylase activity.

4. Once it has been established that the methylase gene has been cloned, the clone is assayed for HphI restriction endonuclease activity. If the HphI gene was contained on the fragment which had the methylase gene and behaved as all Haemophilus strains mentioned in the abstract, one could then skip to Step 10 which describes further genetic manipulations necessary for overexpression and stabilization of the endonuclease gene. However, in accordance with the present invention, it has been found that even if present, the restriction gene is not expressed without following Steps 5–8.

5. The lack of restriction activity usually indicates that either the restriction gene is not linked to the methylase gene or that it is not cloned intact with the methylase gene, or it is cloned intact but not expressed. In order to determine which possibility is actually the case, the N-terminus of the endonuclease was sequenced and the information was used to generate DNA probes. The probes can be used in hybridization experiments to map the gene on the chromosome and to determine which restriction fragments, when cloned, will contain both the methylase and endonuclease genes. The probes can also enable one to directly screen libraries for the endonuclease gene as well as sequence the endonuclease gene once it has been cloned.

6. Southern blot analysis identified a number of restriction fragments which contain the intact HphI gene. New libraries were constructed by digesting genomic DNA from *H. parahaemolyticus* with restriction endonucleases identified in the Southern blot. A ClaI library was predicted to contain the entire restriction-modification system and, therefore, it could be obtained by methylase selection, provided that there was methylase activity occuring with this clone. A PstI-EcoRI library was expected to carry only the restriction gene intact and positive clones from this library would be identified by screening the library with an oligonucleotide that will hybridize to the DNA sequence of the N-terminus of the HphI endonuclease. This library was constructed in an *E. coli* strain premodified with an HphI methylase on a plasmid compatible with the pUC19/PstI-EcoRI library. Clones are identified from these libraries and are analyzed for their ability to produce HphI endonuclease.

7. In accordance with the present invention, it has been found that clones carrying the HphI restriction endonuclease gene cannot be identified by the usual crude cell extract assay. Therefore, in order to achieve gene expression, new transcription elements are introduced upstream from the HphI restriction gene by means of DNA amplification. DNA primers are designed to amplify the entire HphI endonuclease gene. In one case, the forward primer has the following elements: a SphI cloning site, a stop codon in frame with the lac Z gene, E. coli consensus strong ribosome binding site and spacer sequence between the ribosome binding site and the ATG start codon of the HphI endonuclease. The 3' (reverse) primer was designed to hybridize to the area adjacent to the polylinker region of pUC19 providing the amplified gene with a PstI cloning site. The other HphI gene amplification involved a forward primer that contained an NcoI cloning site and a 3' (reverse) primer with a BglII cloning site.

8. The amplified DNA's are cleaved by their cloning site restriction enzymes and ligated into expression vectors which have been previously cleaved by the same enzymes. Transformations are made with the ligated DNA's into competent cells carrying an HphI methylase gene for pre-protecting the cellular DNA against HphI digestion. Vectors carrying the correct amplified DNA inserts are identified by miniprep procedures.

9. Clones are grown in media containing the appropriate antibiotics to maintain the plasmids and grown following conditions that have been determined to maximize endonuclease production in the cells. The cultures are harvested by centrifugation, resuspended in sonication buffer, and lysed by sonication. The extracts are clarified by centrifugation and assayed for HphI endonuclease activity.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE 1

1. Purification of *Haemophilus parahaemolyticus* chromosomal DNA:

2 grams of *Haemophilus parahaemolyticus* cell paste was resuspended in 16.5 ml TE-10 (10 mM Tris-HCl (pHB), 10 mM EDTA) containing 15 mg Lysozyme and incubated for 1 hr at 37° C. The cell suspension was then lysed by adding 2 ml of 10% SDS and incubating for 15 min at 65° C. Following this incubation, 4 ml of 5M NaClO$_4$ was added and gently mixed. The solution was then extracted with 20 ml of chloroform:isoamyl alcohol (24:1) and the viscous upper layer was collected following a 10 min, 12 krpm centrifugation. The upper layer was re-extracted with 10 mls ether and dialyzed for 48 hr against TE buffer (1 mM EDTA, 10 mM Tris-HCl pH 8) with 6 changes of buffer. The 15 ml of dialyzed DNA was treated with 200 µl RNase (10 mg/ml) for 2 hr at 37° C. and then concentrated by precipitating with 0.55 vol of isopropyl alcohol and NaCl to a final concentration of 0.4M. The DNA was resuspended in TE buffer for a final DNA concentration of 400 µg/ml.

2. Partial digestion of *H. parahaemolyticus*:

15 µg *H. parahaemolyticus* DNA was diluted into 0.5 ml restriction endonuclease digestion buffer (50 mM NaCl, 100 mM Tris-HCl, 10 mM MgCl$_2$, 0.025% Triton X-100 (pH 7.5)). The solution was dispensed into 5 tubes, 100 µl per tube. Each tube was labeled 9, 6, 3, 1, or 0.7 and the corresponding number of units of EcoRI was added to the tubes. The tubes were incubated for 1 hr at 37° C. The reactions were terminated by phenol chloroform extractions (1:1, v/v) followed by chloroform extraction (1:1, v/v) and isopropyl precipitation. The digests were each resuspended in 50 µl TE and 5 µl from each digest was analyzed by agarose gel electrophoresis. Seven additional digestion series were performed in a similar manner to EcoRI using HindIII, PstI, Sau3AI, BglII, HpaII, NheI, and SpeI.

3. Ligation and transformation:

2.0 µg (7.5 µl) of EcoRI-digested *H. parahaemolyticus* DNA was mixed with 1.0 µg (4 µl) of EcoRI-cleaved and dephosphorylated pUC19 (ATCC No. 37254). 2 µl of 10× ligation mix (500 mM Tris, (pH 7.5), 100 mM MgCl$_2$, 100 mM DTT, 5 mM ATP) was added, plus 5.5 µl of sterile distilled water to bring the final volume to 19 µl. 1 µl (400 units) of T4 DNA ligase was added and the mixture was incubated at 16° C. for 4 hours. 10 µl of the ligated DNA was used to transform, by electroporation, the *E. coli* strain ER 1398 (Raleigh, E. A. et al. (1987) *Meth. Enzymol.* 152, 130–141, the disclosure of which is hereby incorporated by reference herein) as follows: 1 liter of LB medium was inoculated 1:500 with an overnight culture of *E. coli* ER 1398 cells. When the culture reached mid-log phase (Klett= 65), the cells were harvested by centrifugation at 4 krpm for 15 min in a Beckman J2-21 centrifuge with a JA-14 rotor. The supernatant was decanted and the cells resuspended in 1 liter sterile distilled H$_2$O at 4° C. Cells were harvested as described above and resuspended a third time in 20 ml sterile distilled H$_2$O containing 10% glycerol at 4° C. Cells were harvested as above and resuspended a final time in 2 ml sterile distilled H$_2$O containing 10% glycerol at 4° C. The cell density at this point was approximately 3×10$^{10}$ cells/ml. The cells were used immediately for the electroporation of the ligated DNA. 10 µl of the ligated DNA was diluted in 40 µl sterile distilled H$_2$O and mixed with 40 µl cells on ice for 1 min. Current was applied to the mixture with a Bio-Rad Gene Pulser apparatus set to 25 µFD and 200 ohm resistance with a 2.5 kV pulse. The electroporated cells were resuspended in 1 ml LB and incubated at 37° C. for 1 hr. The 1 ml cell suspension was then used to inoculate 20 ml LB containing 100 µg/ml ampicillin and was incubated overnight at 37° C. Seven additional ligations and transformations were made in a similar manner using *H. parahaemolyticus* DNA digested with HindIII, PstI, Sau3AI, BglII, HpaII, NheI, and SpeI.

4. preparation of plasmid libraries:

The primary plasmid libraries were prepared using the following miniprep procedure: Each 20 ml overnight culture of transformed cells was centrifuged at 5 krpm for 10 minutes; the supernatant was discarded and the cell pellet was resuspended in 2.0 ml of 25 mM Tris, 10 mM EDTA, 50 mM glucose, (pH 8.0), containing 1 mg/ml lysozyme. After 10 minutes at room temperature, 4.0 ml of 0.2M NaOH, 1% SDS was added to each tube and the tubes were shaken to lyse the cells, then placed on ice. Once the solutions had cleared, 3 ml of 3M sodium acetate, pH 4.8, was added to each and shaken. The precipitates that formed were spun down at 15 krpm, 4° C. for 10 minutes. Each supernatant was poured into a centrifuge tube containing 6 ml of isopropanol and mixed. After 10 minutes at room temperature, the tubes were spun at 15 krpm for 10 minutes to pellet the precipitated nucleic acids. The supernatants were discarded and the pellets were air-dried at room temperature for 30 minutes. Once dry, the pellets were resuspended in 850 µl of 10 mM Tris, 1 mM EDTA, (pH 8.0). 75 µl of 5M NaCl was added to each and the solutions were transferred to Eppendorf tubes containing 575 µl of isopropanol, and again precipitated for 10 minutes at room temperature. The tubes were then spun at 1.5 krpm for 45 seconds in a microfuge, the supernatants were discarded and the pellets were air-dried. The pellets were then dissolved in 500 µl of 10 mM Tris, 1 mM EDTA, (pH 8.0), containing 100 µg/ml RNase and incubated for 1 hour at 37° C. to digest the RNA. The DNAs were precipitated once more by the addition of 50 µl of 5M NaCl followed by 350 µl of isopropanol. After 10 minutes at room temperature, the DNAs were spun down by centrifugation for 45 seconds, the supernatants were discarded and the pellets were each redissolved in 250 µl of 10 mM Tris 1 mM EDTA, (pH 8.0). The 250 µl volumes of DNA were extracted with equal volumes of phenol/chloroform (1:1, v/v) then precipitated with isopropanol and the dried pellets were resuspended in 250 µl TE. The plasmid miniprep libraries were analyzed by agarose gel electrophoresis and had DNA concentrations of 40–200 µg/ml.

5. Methylase Selection of plasmid libraries:

1 µg of each plasmid library was diluted into tubes containing 48 µl of 50 mM potassium acetate, 20 mM Tris acetate, 10 mM magnesium acetate, 1 mM dithiothreitol (pH 7.9). 100 units of HphI restriction endonuclease were added to each tube and the reactions were incubated for 2 hr at 37° C. Following the digestions, E. coli ER1398 cells were transformed with DNA from each reaction in the following manner: 10 µl (0.2 µg) of a digest was mixed with 25 µl of 50 mM NaCl, 5 mM Na$_3$Citrate, 67 mM CaCl$_2$ and 50 µl competent E. coli ER1398 cells on ice for 2 min., then at 42° C. for 3 min, then on ice for 2 min. The transformed cells were then plated onto Luria-agar plates containing 100 µg/ml ampicillin and incubated at 37° C. overnight. Between 5 and 20 colonies were picked from among the survivors of each library. Each colony was inoculated into 10 ml LB broth containing 100 µg ampicillin and grown overnight at 37° C. Each of the plasmids present in the 70 isolates was purified by the miniprep purification procedure previously described in the plasmid library section, adjusting the solution volumes in half to accomodate 10 ml cultures.

6. Identification of HphI methylase clones:

Twenty-three of seventy plasmids that were analyzed were found to be resistant to HphI digestion but all of these clones failed to synthesize HphI endonuclease. Eleven of the clones, all approximately 2.9 kb in size, were isolated from the EcoRI library. The other twelve clones, all approx. 2.3 kb, came from the Sau3AI library. Restriction enzyme mapping of the clones recovered from the two libraries revealed that the 2.3 kb clone was completely contained within the 2.9 kb EcoRI clone (FIG. 2).

7. Determination of the amino terminus of the HphI endonuclease gene:

The HphI endonuclease protein was purified to near homogeneity from H. parahaemolyticus by a combination of protein purification techniques including Affigel, DEAE-Flow Thru, Heparin-Sepharose, Phosphocellulose and Heparin TSK FPLC columns. The molecular weight of the HphI endonuclease was determined to be approximately 40 kd based on SDS-polyacrylamide gel analysis. The amino terminus sequence of the HphI endonuclease was obtained using Applied Biosystem's 470A protein sequencer. The amino acid sequencing was carried out to 24 residues and a degenerate DNA oligonucleotide was made based on the first 6 residues of the amino acid sequence: Met Gln Ile Tyr Glu Thr (FIG. 3).

8. Genomic mapping of the N-terminus of the HphI endonuclease gene:

The Southern blot technique (Southern, E., J. Mol. Bio., 98:503 (1975), the disclosure of which is hereby incorporated by reference herein) was used to determine the location of the endonuclease gene relative to the cloned methylase gene and to determine new libraries to make in order to isolate the endonuclease gene on DNA fragments judged to be of suitable size for cloning. The DNA used to probe the Southern blot was the degenerate oligonucleotide described in section 7 of Example 1 which was end-labeted with $^{33}$Phosphorus. The DNA's which were used in the Southern blot were H. parahaemolyticus DNA digested individually with BstBI, PstI, NdeI, HindIII, XmnI, SphI, ScaI, PvuII, FspI, BglII, AvaI, ClaI, AccI, AlwnI, NruI and the cloned HphI methylase DNA on the EcoRI and Sau3AI fragments digested with HindIII. Results from the Southern blot experiments revealed that a ClaI library would yield the endonuclease gene and the previously isolated methylase gene together on approximately a 6 kb fragment and that a PstI-EcoRI library would isolate the endonuclease gene on a 2.4 kb fragment. The Southern blot also revealed that the N-terminus of the endonuclease was not present on the EcoRI and Sau3AI clones containing the HphI methylase gene.

9. Isolation of HphI endonuclease gene:

ClaI and PstI-EcoRI libraries were made in the same manner as the EcoRI library described in sections 2–4 of Example 1 with the only differences being that 1) the ClaI library was made with ClaI cleaved and dephosphorylated pACYC184 plasmid (ATCC#37033) and required 34 µg/ml: chloramphenicol instead of ampicillin in the growth medium 2) the PstI-EcoRI library was transformed into E. coli ER1398 strain premodified with a pACYC184 plasmid containing the HphI methylase on the 2.3 kb Sau3AI DNA fragment. This library required both 34 µg/ml chloramphenicol and 100 µg/ml ampicillin in the growth medium. The ClaI library was methylase-selected in the manner described in section 5 of Example 1 and 6 of 21 survivors from the methylase selection exhibited methylase activity but no endonuclease activity. A Southern blot hybridization was done on the 6 methylase positive clones and all 6 of these hybridized to the degenerate oligonucleotide indicating that they contained the HphI restriction gene but did not make any gene product.

Colonies transformed by the PstI-EcoRI library were transferred to nitrocellulose filters by contact-lifts. The filters were immersed in 0.5M NaOH, 2M NaCl for 30 sec.; 0.5M Tris-HCl, (pH 7.5), 3M NaCl for 1 min; 0.3M NaCl, 0.03M Na$_3$Citrate for 10 sec. The filters were air-dried, and then baked in a vacuum-oven at 80° C. for 30 min. Following 1 hr. prehybridization, the filters were probed with the radioactively-labeled degenerate oligonucleotide described in section 7. The filters were air-dried and then autoradiographed overnight. Of approximately 2000 colonies screened, 14 colonies appeared to hybridize to the oligonucleotide probe. Minipreps were done on these potential positives as described in section 4 of Example 1, modifying the procedure for 10 ml cultures, and plasmids were analyzed on Southern blots probed by the degenerate oligonucleotide made to the endonuclease. Southern blot results revealed that 1 of the 14 plasmids contained a 2.4 kb insert that hybridized to the N-terminus of the endonuclease gene. Crude cell extracts made with the single positive 2.4 kb clone did not contain any detectible endonuclease activity. FIG. 4 depicts the restriction enzyme maps for the two types of clones containing the HphI endonuclease gene.

10. Amplification of the HphI endonuclease gene:

With the recovery of two new clones both of which contained the beginning of the HphI endonuclease and enough DNA to encode for the entire HphI endonuclease gene yet made no detectible HphI, it was necessary to devise a way in which to achieve HphI expression in *E. coli* DNA sequence of the beginning of the HphI endonuclease was determined by dideoxy sequencing using the Klenow fragment of DNA Polymerase I (New England Biolabs, Inc., Beverly, Mass.) with the degenerate oligonucleotide (section 7) as the initial primer. The sequence information was utilized in designing primers for DNA amplification. These amplifications generated the HphI endonuclease gene apart from its native transcription elements and with a region to link up the gene to transcription elements that are known to achieve gene expression in *E. coli*. The amplification reaction mixes were made by combining:

5 µl 10× Vent buffer:
100 mM KCl, 200mM Tris-HCl(pH 8.8)
100 mM (NH$_4$)$_2$SO$_4$, 20 mM MgSO$_4$, 1% Triton X-100
1 µl 10 µM primer #3 or #1233
1 µl 10 µM primer #1 or #2.
2 µl dNTP mix (5 mM conc.)
2 plasmid #pUC19-HphR2-3 (10 ng pUC19 containing 2.4 kb PstI-EcoRI DNA fragment)
1.5 µl 100 mM MgSO$_4$
2 µl Vent(exo-) polymerase (2 u/µl) New England Biolabs cat #257)

Primer #1 (SEQ ID NO:3):
5'GCACTAAGCTTATGCATGCATTAACTT-TAAGGAGGATATAAC
CATGGAAATTTATGAAACTTATTGGGAAATTTACT 3'

Primer #2 (SEQ ID NO:4):
5'GCACTAAGCTTATGCATGCATTAACTT-TAAGGAGGATATAAC
CATGCAAATTTATGAAACTTATGGGAAATTACT 3'

Primer #3 (SEQ ID NO:5):
5'CTGCGAGATCTAGCTTGCATGCCTGCAG 3'

NOTE: Primer #1 was used in conjunction with reverse primer 3 to make HphI R gene #1;

Primer #2 was used in conjunction with reverse primer NEB #1233 to make HphI R gene #2

The mix was then run through the following polymerase chain reaction amplification conditions as follows:

95° C. 1 min
62° C. 1 min
72° C. 4 min
20 cycles

15 µl aliquots of both PCR reaction products (FIG. 5) were analyzed on a 1% agarose gel. In both samples, a single band, 1.9 kb in size was observed.

Figure 6A:
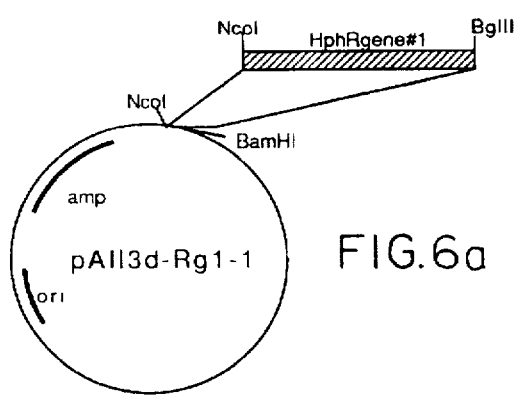
FIG. 6a is the DNA construct of clone pAII3d-Rg1-1 used in HphI gene expression.
Figure 6B:
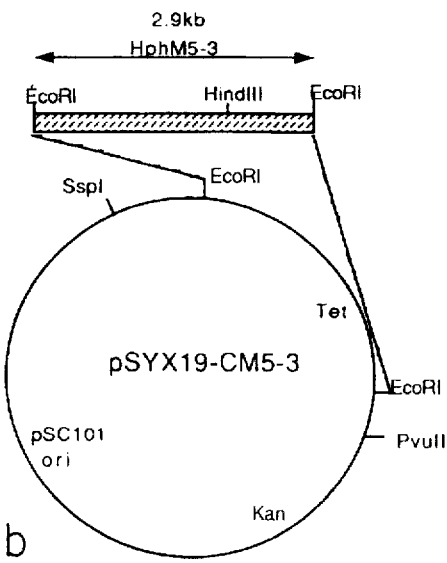
FIG. 6b is the DNA construct used in pre-modification of cells for HphI gene expression using clone pSYX19-CM5-3.
Figure 6D:
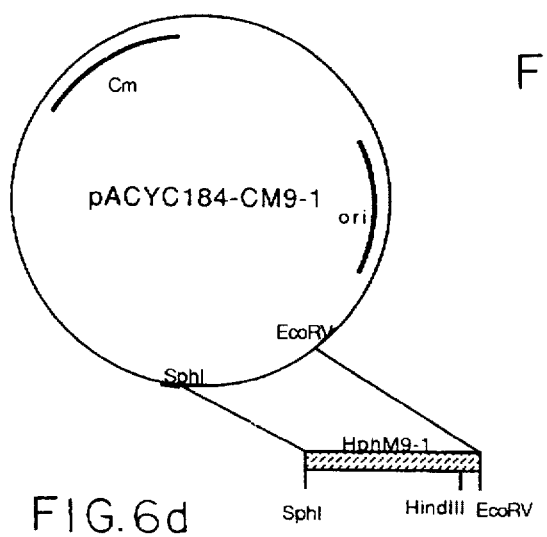
FIG. 6d is the DNA construct used in pre-modification cells for HphI gene expression using clone pACYC184-CM9-1.
Figure 6E:
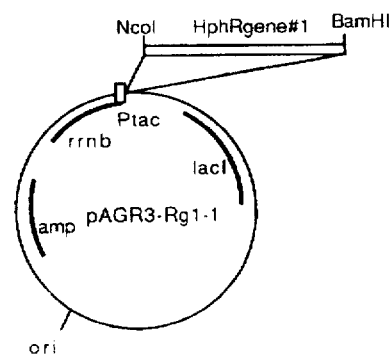
FIG. 6e is the DNA construct of clone pAGR3-Rg1-1 used in expression of HphI.
Figure 6F:
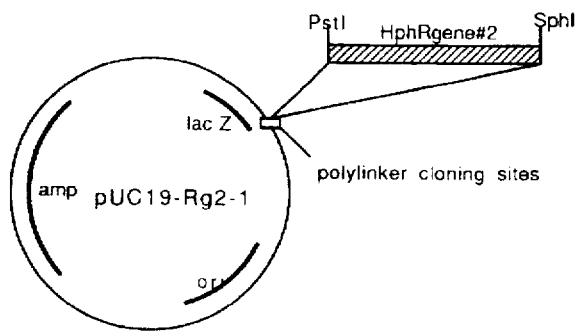
FIG. 6f is the DNA construct of clone pUC19-Rg2-1 used in expression of HphI.
Figure 6C:
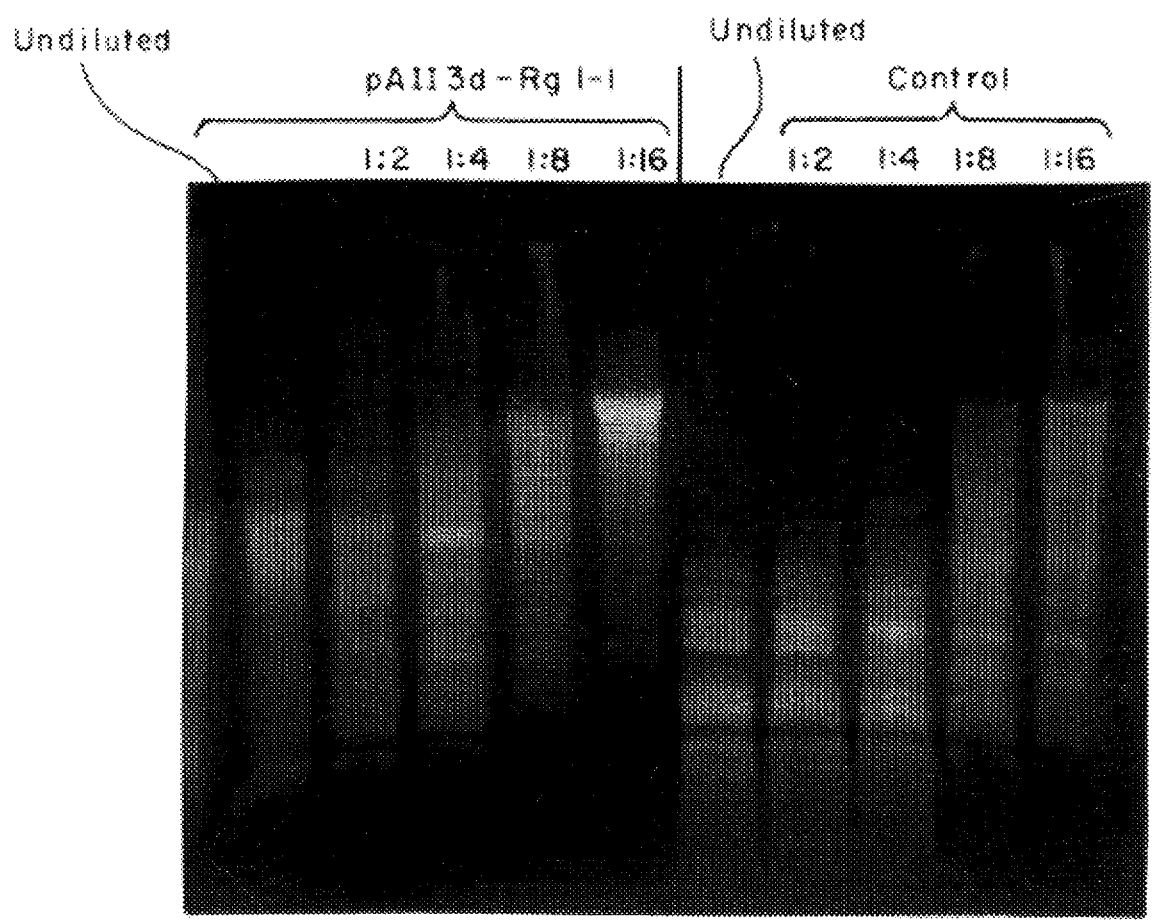
FIG. 6c is a photograph of HphI endonuclease assay from crude extracts of clone pAII3d-Rg1-1 run on an agarose gel.

11. Cloning and expression of HphI endonuclease:

11 A:

HphI R gene #1 was purified by phenol chloroform extraction as described in section 2. 0.2 µg of HphI R gene #1 was digested with NcoI and BglII was phenol chloroform extracted and combined with 0.1 µg of NcoI and BglII-cleaved pAII3d (derivative of pAII17 (Kong, et al. (1993) *J. Biol Chem.* 268, 1965–1975, the disclosure of which is hereby incorporated by reference herein), containing the translation initiation signals from T7 contained in the XbaI-PstI DNA fragment of pET-3d (Studier et al. Methods Enzymol. 1990), the disclosure of which is hereby incorporated by reference herein) in a 10 µl ligation reaction similar to the 20 µl ligation reaction described in section 3. 2 µl of the ligation reaction was transformed into *E. coli* strain ER2252 (Appendix 1) and plated on Luria-agar plates containing 100 µg/ml ampicillin and incubated overnight at 37° C. 14 transformants were selected and their plasmids purified by minipreps and analyzed by 1% agarose gels. 1 of the 14 plasmids contained the HphI R gene #1 (FIG. 6a) and this plasmid was transformed into ER2169 pLys cells (Appendix 2) premodified with pSYX19-CM5-3 (FIG. 6b), containing the HphI cytosine methylase on pSYX19 plasmid (derivative of pSC101, provided by Shuang Xu, New England Biolabs. pSYX19 contains lac Z alpha, pSC101 origin of replication, and a kanamycin resistance gene). The transformants were plated on Luria-agar plates containing 100 µg/ml ampicillin, 34 µg/ml chloramphenicol, and 50 µg/ml Kanamycin and grown overnight at 37° C. 2 colonies were used to inoculate 10 ml Luria broth containing 100 µg/ml ampicillin, 34 µg/ml chloramphenicol, 50 µg/ml kanamycin and incubated at 37° C. At O.D.$_{600}$=0.6, the culture was induced with 50 µl 0.1M IPTG and resumed incubating. At 4 hr post-induction, the cells were pelleted by centrifugation at 6 krpm, resuspended in 1 ml 10 mM KPO$_4$, 0.1 mM EDTA, 0.1 mM β-mercaptoethanol and sonicated for 15 sec. on ice. Following sonication, debris were removed by a 10 min., 1.5 krpm centrifugation and 2 µl of the supernatant were assayed on 1 µg lambda DNA. The clones designated pAII3d-Rg1-1 and pAII3d-Rg1-2, produce 5000 units/g of HphI endonuclease activity (FIG. 6c).

11B:

HphI R gene #2 was purified by phenol chloroform extraction as described in section 2 and digested with SphI and PstI followed by a second phenol chloroform extraction. 0.3 µg of SphI and PstI-cleaved HphI R #2 was ligated to 0.15 µg SphI and PstI cleaved pUC19 in a 10 µl reaction. 2 µl of the ligation was transformed into *E. coli* strain ER2252 premodified with pACYC184 containing HphI methylase on the 2.3 kb Sau3AI fragment (FIG. 6d). 6 of 10 transformants analyzed and assayed for HphI endonuclease activity were positive (FIG. 6f) and 2 of these were selected, identified as pUC19-Rg2-1 & pUC19-Rg2-2 and titered. Both clones produce 5000 units/g.

11C:

0.15 µg of purified HphI R gene #1 digested with NcoI and BglII was combined with 0.1 µg of NcoI and BamHI-cleaved pAGR3 plasmid (Appendix 3) in a 10 µl ligation reaction similar to section 11 A. Example 1.2 µl of the ligation reaction was transformed into *E. coli* strain ER2252 described in section 11B, Example 1.14 transformants were selected, their plasmids analyzed, 4 had the correct construct (FIG. 6e) and were assayed for HphI endonuclease activity. All 4 clones were estimated to make approximately 750 units/g of HphI. One of these clones, designated pAGR3-Rg1-1, was selected and used for further experiments.

Figure 7:
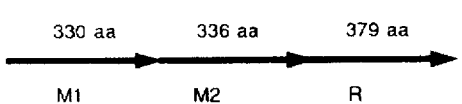
FIG. 7 is the gene organization of the HphI restriction-modification system.

12. Sequencing of the HphI Restriction-Modification System:

Questions concerning the stability and efficiency of the HphI endonuclease clones necessitated sequencing the genes that had been isolated. Sequencing by dideoxy method as described in section 10, revealed the existence of two methylase genes: one cytosine methylase gene, which was the one initially identified by methylase selection and used for all of the premodification procedures in Example 1, and one adenine methylase gene, which, due to the nature of the constructs in section 11- A, B, and C, was unable to express in these constructs. FIG. 7 illustrates the sizes and organization of the genes comprising the HphI restriction-modification system.

Appendix 1—Construction of ER2252

Strains used:

| Strain | Genotype | Reference or construction |
|---|---|---|
| 71-18 | F′ proA+B +lacI^q Δ(lacZ)M15 /I− Δ(lac-proAB) thi supE | Yanisch-Perron, C., Vieira, J. & Messing, J. (1985). Improved M13 phage cloning vectors and host strains: nucleotide sequences of the M13mp18 and pUC19 vectors. Gene 33:103–119, the disclosure of which is hereby incorporated by reference herein. |
| ER1996 | F− I−fhuA2 Δ(argF-lac)U169 supE44 e14− trp-31 his-1 rpsL104 xyl-7 mtl-2 metB1 Δ(mcrC-mrr)114:IS10 | Mi, S. & Roberts, R. J. (1992). How M. MspI and M. HpaII decide which base to methylate. Nucleic Acids Res. 20:4811–4816, the disclosure of which is hereby incorporated by reference herein. |
| ER2250 | F′ proA+B +lacI^q Δ(lacZ) M15 zzf::mini-Tn10 (Kan^R)/I−trp-31 his-1 fhuA2 rpsL104 supE44 xyl-7 mtl-2 metB1 e14− Δ(mcrC-mrr) 114::IS10 Δ(argF-lac)U169 | 71-18/pNK862 (Kan^R mini-Tn10) × ER1996 (mating)→ Kan^R Strep^R Amp^S |
| ER1991 | F− I− Δ(argF-lac)U169 supE44 e14− rfbD1? relA1? endA1 spoT1? thi-1 Δ(mcrC-mrr)114:IS10 | Fomenkov, A., Xiao, J.-P., Dila, D., Raleigh, E. & Xu, S.-Y. (1994). The "endo-blue method" for direct cloning of restriction endonuclease genes in E. coli. Nucleic Acids Res. 22:2399–2403, the disclosure of which is hereby incorporated by reference herein. |
| ER2252 | F′ proA+B+ lacI^q Δ(lacZ) M15 zzf::mini-Tn10 (Kan^R)/I− D(argF-lac)U169 supE44 e14− rfbD1? relA1? endA1 spoT1? thi-1 Δ(mcrC-mrr) 114::IS10 | ER2250 × ER1991 (mating)→ Kan^R, prototrophic | pNK862 (miniTn10 delivery vehicle) and its use are described in Way, J., Davis, M., Morisato, D., Roberts, D. & Kleckner, N. (1984), the 5 disclosure of which is hereby incorporated by reference herein. New Tn10 derivatives for transposon mutagenesis and for construction of lac operon fusions by transposition. Gene 32:369–79, the disclosure of which is hereby incorporated by reference herein.

Matings and phenotype tests were carried out as described in Miller, J. W. (1972). Experiments in Molecular Genetics Cold Spring Harbor Laboratories, Cold Spring Harbor, N.Y, the disclosure of which is hereby incorporated by reference herein.

Appendix 2—Construction of ER2169

Strains used:

| Strain | Genotype | Reference or construction |
|---|---|---|
| BL21 (DE3) | E coli B [F−] gal ompT [lon] (IDE3=l sBamH1° ΔEcoRI-B int::lacI::PlacUV5::T7 gene1 i21 Δ nin5) | BL21(DE3) × P1vir(ER1489)→ Tet^R (McrB−). |

| Strain | Genotype | Reference or construction |
|---|---|---|
| ER1439 | F− I− trp-31 his-1 argG6 rpsL104 fhuA2 Δ(lacZ)r1 supE44 xyl-7 mtl-2 metB1 Δ(mcrC-mrr)102::Tn10 | Raleigh, E. A., Trimarchi, R. & Revel, H. (1989). Genetic and physical mapping of the mcrA (rg1A) and mcrB (rg1B) loci of Escherichia coli K-12. Genetics 122:279–296, the disclosure of which is hereby incorporated by reference herein. (Backcross strain ER1486 reported). |
| ER2169 | E coli B [F−] Δ(mcrC-mrr) 102::Tn10 gal ompT [lon] (IDE3=l sBamH1° ΔEcoRI-B int::lacI::PlacUV5::T7 gene1 i21 Δnin5) | BL21(DE3) × P1vir(ER1489)→ Tet^R (McrB−). |

Genotype notations in brackets are wild type states for E. coli B but are different from familiar K-12 wildtype states. Genotype conventions are otherwise as in Demerec, M., Adelberg, E. A., Clark, A. J. & Hartman, P. E. (1966). A proposal for a uniform nomenclature in bacterial genetics. Genetics 54:61–76, the disclosure of which is hereby incorporated by reference herein.

Transduction and phenotype tests were carried out as described in Raleigh et al (1989), the disclosure of which is hereby incorporated by reference herein.

Construction data from ER notebook "Strain constructions" 22 Feb. 1991–28 Feb. 1991

Appendix 3 pAGR3 was constructed by inserting the EcoRI fragment containing the lacI^q gene from pACYC184/lacI^q (J. C. Wang, L. J. Peck and K. Becherer (1983) Cold Spring Harbor Symposium 47:85–91, the disclosure of which is hereby incorporated by reference herein) into the EagI site of pRS415 (R. W. Simons, R. Houman and N. Kleckner (1987) Gene 53:85–96, the disclosure of which is hereby incorporated by reference herein) with the lacIq gene in the opposite orientation to the beta-lactamase gene on pRS415. Prior to the ligation, the termini of both DNA fragments were converted to blunt ends using the Klenow fragment of DNA polymerase I. The pRS415/lacI^q construct was cleaved with EcoRI and SalI, and the fragment bearing the replication origin ligated to a synthetic duplex (below) containing the Ptac promoter, a ribosome binding site, and a multiple cloning site. This final construct was named pAGR3.

Expression plasmid pAGR3:5910 bp.
Promoter and cloning site map (SEQ ID NO:6):

```
                       lac operator
  1   GAATTGTGAGCGCTCACAATTCTAGGATGTTAATTGCGCCGACATCATAA -35 region
 51   CGGTTCTGGCAAATATTCTGAAATGAGCTGTTGACAATTAATCATCGGCT -10 region       lac operator                      rbs
101   CGTATAATGTGTGGAATTGTGAGCGGATAACAATTTCACACAGGAAACAG start
151   ACCATGGTGAATTCTAGAGCTCGAGGATCCGCGGTACCCGGGCATGCATT
          NcoI   EcoRI XbaI SacI XhoI BamHI SacII KpnI SmaI    BstBI 201   CGAAGCTTCCTTAAGCGGCCGTCGACCGATGCCCTTGAGAGCCTTCAACC
          HindIII  AflII   EagI  SalI
```

Plasmid pAGR3 is an expression vector which includes several elements:

1. A synthetic tac promoter coupled to a symmetric synthetic lac operator sequence
2. A lac ribosome binding site
3. A polylinker for cloning, with the ATG within the NcoI site being about seven nucleotides downsteam of the ribosome binding site
4. A copy of the lacIq gene to provide repression of the tac promoter
5. The replication origin from pBR322
6. Ampicillin resistance gene
7. A four-fold copy of the ribosomal transcription terminator upstream of the tac promoter. These transcription terminators lower the basal level of transcription by reducing read-through transcription from upstream promoters.

EXAMPLE 2

Construction of an Expression System Including the Adenine Methylase

Our theory was that the level of HphI restriction endonuclease production was low due to inadequate protection of the host DNA by the cytosine methylase and no protection at all by the adenine methylase. In the absence of adequate protection against digestion by the HphI endonuclease produced in the cells, the cells would either die or mutate the endonuclease gene to an inactive form or select for cells that had lost the endonuclease plasmid. One approach for expressing the HphI endonuclease was to aim for better expression of the methylase genes. The first part of this project involved subcloning the adenine methylase gene which, up to this point, had not been included in constructs producing the endonuclease or cytosine methylase, and to insert it behind a relatively strong promoter in several vectors of varying copy number. The second tack was to provide a better ribosome binding site for the two methylase genes in an attempt to increase their translation efficiency in E. coli.

1. Amplification of the Adenine Methylase Gene.

The adenine methylase gene was amplified by the polymerase chain reaction in order to subclone it into two vectors of differing copy number, pACYC184 and pSYX20, as well as a third vector, pCEF8. The latter vector is based upon pSYX20 but also contains the T7 lysozyme gene for use in systems expressing genes controlled by the T7 RNA promoter and transcribed by T7 RNA Polymerase.

Two primers were produced for the amplification. The first (5' primer, #4) introduced a ribosome binding site (rbs) 10 nucleotides upstream from the transcription initiation codon, providing a better E. coli rbs than that which existed in the native DNA. This primer overlaps a MunI site 33 nucleotides upstream from the start of the adenine methylase gene. The second (3' primer, #5) introduces a BamHI site 42 nucleotides downstream from the stop codon of the Adenine methylase gene (for a description of pSYX20 and pCEF, see Example 2, section 2).

The amplification reaction mixes were made by combining:

10 µl 10× Vent buffer: 100 mM KCl, 200 mM Tris-HCl (pH 8.8), 100 mM (NH4)2SO4, 20 mM MgSO4, 1% Triton X-100
3.8 µl 2.53 µM primer #4
2.2 µl 3.09 µM primer #5
1.6 µl dNTP mix (25 mM conc.)
1.3 µl plasmid pACYC184-HphRM6-7 (90 ng)
4.0 µl 100 mM $MgSO_4$
76.1 µl sterile distilled water (for a final volume of 100 µl)
1 µl Taq DNA Polymerase (0.5 u/µl) Promega cat#1861)

Primer #4 (SEQ ID NO:7):
5'AGCTCAAGCAATTGCCGAAGCAGTGT-TAAAAAGGAA

Primer #5 (SEQ ID NO:8):
5'ACGCTCTGTGTTGGATCCGTATTCA

The mix was preheated to 95° C. then run through polymerase chain reaction amplification as follows:

95° C. 1 min
52° C. 30 sec
72° C. 70 sec

The Taq DNA Polymerase (Promega; Madison, Wis., Cat# M186A) was added during the first cycle at the 52° C. incubation. The reactions were allowed to continue for 20 cycles. 10 µl were analyzed on a 1% agarose gel. A 1 kb band was observed. The PCR fragment was extracted once with an equal volume of phenol:chloroform (1:1) and twice with an equal volume of chloroform. It was precipitated with 0.1 volume of 3M NaOAc and 2.5 volumes of ethanol, and collected by centrifugation in a microcentrifuge for 30 min at 4° C. The fragment was resuspended in TE buffer (10 mM Tris-HCl, (pH 8.0 at room temp.), 1 mM EDTA) and the amount of DNA was quantitated by comparing it with standards of known concentration on a 1% agarose gel.

The PCR product was digested with MunI and either BamHI or NlaIII. The DNA digested with MunI and BamHI produced a 1085 bp fragment of HphI DNA which was inserted into pLITMUS38 (New England Biolabs, cat#306-38) digested with MunI and BamHI and dephosphorylated with CIP; the products of this ligation were called pCDX. The PCR fragment cut with MunI and NlaIII produced a 972 bp fragment which was inserted into pLITMUS38 digested with MunI and SphI and dephosphorylated; the products of this ligation were called pCDY. pLITMUS38 is a pUC-based plasmid with a polylinker containing a large selection of restriction enzyme recognition sequences. The PCR DNA was ligated into the appropriate plasmid in a 3:1 molar ratio (insert:vector) in a 10 µl reaction volume in 1× T4 DNA ligase buffer [final concentration: 50 mM Tris-HCl (pH 7.8), 10 mM MgCl$_2$, 10 mM DTT, 1 mM ATP, 25 µg/ml BSA] plus 400 units of T4 DNA ligase at 17° C. for 6 hours. An aliquot of competent ER2420 (RR1 tonA1) cells was transformed with a sample of the ligation mixtures. The transformation mixture was plated on Luria agar plates containing 100 µg/ml ampicillin and incubated overnight at 37° C. Eighteen of the resulting single colonies were grown up in tubes containing 2 ml Luria broth plus 100 µg/ml ampicillin. Plasmid DNA was collected from the cells by a modifed Boiling Lysis Miniprep procedure (modified from Maniatis, *Molecular Cloning*, Cold Spring Harbor, pp. 366-367 (1982), the disclosure of which is hereby incorporated by reference herein).

Two microliters of the DNA from each colony were digested with HphI in a 25 µl reaction containing 1× NEBuffer #4 [final concentration, 20 mM Tris-acetate, 10 mM MgOAc, 50 mM KOAc, 1 mM DTT, pH 7.9 at 25° C.)], 100 µg/ml BSA and 6 units of HphI at 37° C. for 60 min. Stop buffer was added to the reactions and the digested DNA was run on a 1% agarose gel alongside undigested DNA to determine which colonies' DNA was methylated and therefore protected from digestion by HphI. Sixteen of 18 ampicillin-resistant pCDX colonies appeared to have the correct-sized insert; the DNA of 14 of those 16 was protected from HphI digestion. One of these colonies was named pCDX1 and was used for future experiments. Sixteen of 18 ampicillin-resistant pCDY colonies appeared to have the correct-sized insert, but none of the DNA from the pCDY colonies was protected from digestion by HphI. Later sequencing determined that the end of the adenine methylase gene was not contained in the MunI to NlaIII insert in pCDY.

2. Subcloning the Adenine Methylase Gene

The HphI adenine methylase gene was subcloned into several other vectors with non-colE1 origins to avoid incompatibility problems later on between the adenine methylase plasmid and the endonuclease gene cloned into pAII3d or pAGR3, both of which contain the colE1 origin.

A large quantity of pCDX1 DNA was prepared by CsCl density centrifugation of DNA obtained from a 1 l culture of ER2420 containing pCDX1, grown in Luria Broth supplemented with 100 µg/ml ampicillin. The culture was inoculated using a single colony of pCDX1 in ER2420, and was allowed to grow for 17 hours at 37° C. Plasmid DNA was collected by alkaline lysis and purified by CsCl-density gradient purifications; both methods were modified from Maniatis, *Molecular Cloning*, pp. 90-94 (1982), the disclosure of which is hereby incorporated by reference herein. The amount of DNA was quantitated by ultraviolet spectrophotometry at 260 nm.

A fragment containing the adenine methylase gene was isolated from pCDX1 in the following manner: 12 µg of pCDX1 were digested with 72 units of MunI in a 60 µl reaction containing 1× buffer #2 (10 mM Tris-HCl, 10 mM MgCl$_2$, 50 mM NaCl, and 1 mM DTT (pH 7.9 at 25° C.)) and 100 µg/ml BSA. The 5' overhang was filled in with T4 DNA Polymerase. The reaction volume was increased to 160 µl by adding 10 µl of T4 DNA Polymerase Buffer (final concentration =50 mM NaCl, 10 mM Tris-HCl, 10 mM MgCl$_2$ and 1 mM DTT (pH 7.9 at 25° C.)), 1.0 µl BSA (final concentration 100 µg/ml), 8.0 µl of 2 mM dNTPs (final concentration 0.1 mM each dNTP), 71 µl sterile distilled water and 10 µl (30 units) of T4 DNA Polymerase (from New England Biolabs, Inc.; Beverly, Mass., cat #203). The mixture was incubated at 12° C. for 15 min, heated to 75° C. for 10 min and then extracted once with an equal volume of phenol:chloroform (1:1, v/v) and twice with an equal volume of chloroform. The DNA was precipitated with 0.3M NaOAc and 2.5 volumes of ethanol at −20° C. overnight. The DNA was collected by centrifugation at 4° C. for 60 min, dried, and resuspended in 20 µl of TE. It was then digested with BamHI in a 60 µl reaction containing 1× BamHI Buffer [150 mM NaCl, 10 mM Tris-HCl, 10 mM MgCl$_2$, 1 mM DTT (pH 7.9 at 25° C.)], 100 µg/ml BSA and 20 units of BamHI. The reaction was incubated at 37° C. for 60 min.

The MunI-digested, T4 DNA Polymerase-treated, BamHI-digested fragment was purified away from other bands by agarose gel electrophoresis on a 0.7% Sea Kem GTG agarose gel (FMC BioProducts, Rockland, Me.). The 1200 bp fragment was cut out of the gel and purified away from the agarose in an Elutrap (Schleicher & Schuell, Inc., Keene, N.H.) using the method described by the manufacturer. The solution containing the eluted DNA was collected and the DNA was precipitated with 0.3M NaOAc and 2.5 volumes of ethanol at −20° C. over the weekend.

The fragment containing the adenine methylase was ligated into the following vectors: pACYC184, pSYX20 and pCEF8, all digested with EcoRV and BamHI and dephosphorylated. Vector pACYC184 is a low-copy number plasmid with a p15A origin of replication and chloramphenicol and tetracycline resistance genes. pSYX20 is a pSC101-based plasmid which has been mutagenized (by Shuang-Yong Xu, New England Biolabs, Inc., Beverly, Mass.) to increase the copy number. It contains the kanamycin and tetracycline resistance genes. Plasmid pCEF8 is pSYX20 containing the T7 lysozyme gene for use with the T7 promoter plasmids. In all cases the HphI adenine methylase gene was inserted behind the relatively strong tetracycline gene promoter.

Ligations were performed in 10 µl volumes containing 1 µl of T4 DNA ligase buffer [final concentration: 50 mM Tris-HCl (pH 7.8), 10 mM MgCl$_2$, 10 mM DTT, 1 mM ATP, 25 µg/ml BSA] and 0.5 µl (50,000 units) of concentrated T4 DNA Ligase (New England Biolabs, cat 202C) with a 3:1 molar ratio of insert:vector, keeping the insert concentration at <5 µg/ml and the vector concentration <1 µg/ml. The reactions were done at room temperature for 2-20 hours with the higher concentration enzyme to aid the ligation of the blunt ends.

Competent ER2420 cells were transformed with several µl of each of the above ligation mixtures. The transformed cells were diluted with Luria Broth (1:9) and incubated at 37° C. for 60 min to allow expression of the chloramphenicol or kanamycin resistance genes. The cells were then plated on Luria agar spread with 30 µg/ml chloramphenicol or 50 µg/ml kanamycin and incubated at 37° C. overnight.

Figure 8A:
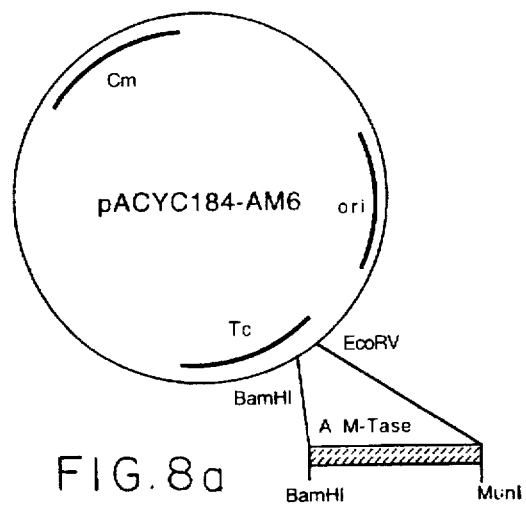
FIG. 8a is the DNA construct used in pre-modification of cells for HphI gene expression using clone pACYC184-AM6.
Figure 8B:
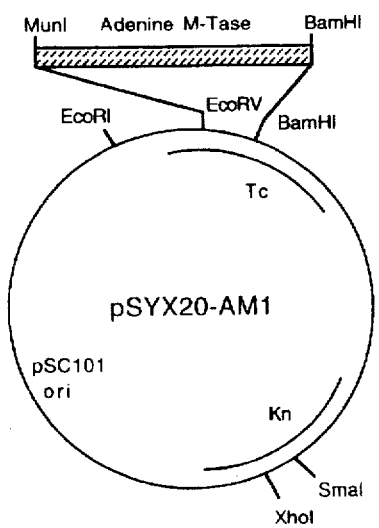
FIG. 8b is the DNA construct used in pre-modification of cells for HphI gene expression using clone pSYX20-AM1.
Figure 8C:
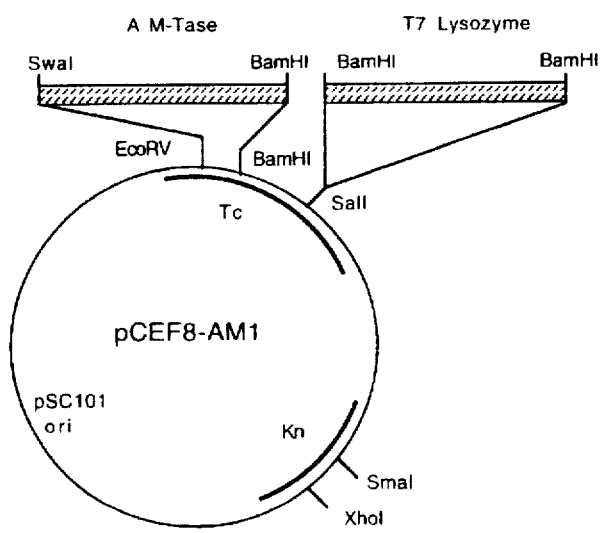
FIG. 8c is the DNA construct used in pre-modification of cells for HphI gene expression using clone pCEF8-AM1.

Approximately 18 antibiotic-resistant colonies from each ligation were screened as above for the correct insert and for resistance to cleavage by HphI endonuclease. A colony from each ligation which had the proper insert and exhibited methylase activity was chosen and named as follows:

pACYC184+adenine methylase=pACYC184-AM6 (FIG. 8a); pSYX20+adenine methylase=pSYX20-AM1 (FIG. 8b); pCEF8+adenine methylase=pCEF8-AM1 (FIG. 8c).

3. Subcloning the Cytosine and Adenine Methylases

Subcloning of the cytosine and adenine methylases into pSYX20. Once the boundaries of the two methylase and one endonuclease gene were confirmed by sequencing, the two methylase genes were subcloned together into pSYX20 under the assumption that, since they overlap in *Haemophilus parahaemolyticus*, transcription might be coupled and sufficient expression of the two genes together might allow for better expression of the endonuclease gene. A SwaI to EcoRV fragment was purified from the pACYC184-HphRM6-7 clone containing approximately 7 kb of *Haemophilus parahaemolyticus* DNA. The SwaI to EcoRV fragment contains 218 nucleotides upstream of the cytosine methylase gene, the complete cytosine and adenine methylase genes and 522 nucleotides of the restriction endonuclease-coding sequence.

5 μg of pACYC184-HphRM6-7 clone were digested in 100 μl reaction volume in 1× buffer H (from Boehringer Mannheim, Münich, Germany) final concentration=50 mM Tris-HCl, 10 mM MgCl$_2$, 100 mM NaCl, 1 mM DTE, (pH 7.5 at 37° C.)) with 100 μg/ml BSA and 25 units of SwaI (Boehringer Mannheim; Mannheim, Germany, cat #1371517) at 25° C. for 40 min. Sixty-two units of EcoRV were added and the tube was transferred to 37° C. for 60 min. The 1600 bp fragment was purified away from the rest of the digestion by electrophoresis in 0.7% Sea Kem GTG agarose and was purified away from the agarose in an Elutrap for 2 hours at 200 volts as above. The fragment was precipitated with ethanol, dried, resuspended in TE, quantitated and ligated into pSYX20 digested with EcoRV and dephosphorylated. The ligation mixture was transformed into competent ER2420 cells and kanamycin-resistant colonies were selected on Luria agar spread with 50 μg/ml kanamycin. Kanamycin-resistant colonies were checked for correct size and orientation of insert as well as resistance of the plasmid to digestion by HphI. The miniprep DNA from one colony filling these criteria was named pSYX20-CM, AM1 (FIG. 8d).

4. Assaying the Cells for HphI Endonuclease Expression

Various combinations of the overexpression constructs were combined in an attempt to increase the production of the restriction endonuclease. Competent ER2420 or ER2497 cells were transformed with one or two methylase plasmids and selected on Luria agar plates containing the appropriate antibiotic(s). Competent cells were made from antibiotic-resistant colonies picked from these plates; these cells were transformed with either pAGR3-Rg1-1 (ER2420 cells) or pAII3d-Rg1-1 (ER2497 cells) and again selected on antibiotic plates. One to several colonies were picked from these plates to assay for endonuclease production.

In most cases, a single colony was sterilely transferred into Luria broth containing the appropriate antibiotics and incubated overnight with shaking at 30° C. or 37° C. In the morning, a portion of the overnight culture was transferred to a larger volume of Luria broth plus antibiotics, and grown with shaking, at the same temperature at which the overnight culture was grown until the culture reached a Klett reading of 100 to 125 (O.D.$_{600}$=0.8 to 1.0). IPTG was added to the culture to a concentration of 0.4 mM to induce transcription of the endonuclease gene, and the culture was returned to the incubator for 2 to 20 hours. The cells were harvested at a specific time after induction, by centrifugation of 50 ml of cells at 5,000 rpm for 8 min at 4° C. An aliquot of the decanted supernatant (hereafter called "SN") was saved for assaying escaped HphI endonuclease activity. This was done in the case of the T7 expression system to indicate whether there was cell lysis occurring. In ER2497 cells, the T7 RNA Polymerase is present in the cells as a lambda lysogen integrated into the chromosome. While not wishing to be bound by theory, it is believed that the lambda lysogen can sometimes induce cell lysis in response to the SOS mechanism of the cells which is turned on by double-stranded DNA breaks, including those induced by restriction endonucleases in under-methylated bacteria. The cell pellet left after the SN was decanted was weighed and then frozen.

Enzyme activity was measured in the frozen pellets and the SNs in the following manner. Pellets were resuspended in 9.7 ml of sonication buffer [10 mM Tris-HCl, (pH 8.0), 1 mM EDTA, 10 mM β-ME]. They were transferred to ice-cold, 15 ml glass Corex tubes containing 0.3 ml of lysozyme [5 mg/ml in sonication buffer] and mixed by inverting. The tubes were allowed to sit on ice for 10–20 minutes and then the cells were sonicated 3 times for 15 seconds at a time using a microtip at a setting of 5, 90% duty, at 24 watts, with continuous bursts. One ml of each sonicated sample was transferred to a 1.5 ml Eppendorf tube and centrifuged for 5 min at full speed (15,000 rpm) to pellet cell debris. The supernatant from this spin will be referred to as "broken cells" hereafter.

HphI restriction endonuclease activity was measured in the SNs and the broken cells. One or 2 μl of SN or broken cells was transferred to a microtiter dish well containing 50 μl of assay buffer [20 mM Tris-Acetate, 10 mM MgOAc, 50 mM KOAc, 1 mM DTT, (pH 7.9 at 25° C.)) plus 20 μg/ml lambda DNA and 100 μg/ml BSA]. The reaction mixture in this well was diluted serially, transferring for example 10 μl from this well into the next well containing 40 μl of assay buffer, then 25 μl from the second well into the third well containing 25 μl of assay buffer, etc. The volumes of the serial dilution were revised as it became evident that a different titration pattern would be more appropriate for the amount of HphI restriction endonuclease present. The microtiter dishes were covered and incubated at 37° C. for 30 min. Stop dye was added to terminate the reaction and the samples were electrophoresed on a 1.0% agarose gel and compared to a complete digest of lambda DNA by purified HphI restriction endonuclease.

5. Experiments performed:

5A:

In the following experiment, endonuclease plasmid DNAs pAGR3-Rg1-2 prepared by different methods were tested for activity. pAGR3-Rg1-1 prepared by CsCl density centrifugation was compared the same plasmid prepared by boiling lysis miniprep procedure ("miniprep DNA"). Similarly, pAII3d-Rg1 μl DNAs prepared by either CsCl density centrifugation or boiling lysis miniprep were compared with each other for activity. ER2420 cells were used for the pAGR3-constructs and ER2497 cells containing pLysS were used for the pAII3d-constructs. The cells were pre-modified with pSYX20-CM,AM1. The cells containing pSYX20-CM,AM1 with or without pLysS and newly transformed with the appropriate endonuclease construct were selected on plates containing 100 μg/ml ampicillin and 50 μg/ml kanamycin (+30 μg/ml chloramphenicol, where pLysS was also present). As is frequently the case in cell lines overexpressing a restriction-modification system, the plates of the transformed cells yielded two sizes of colonies, small and large. It is not unusual to find that the smaller, often sicker, colonies are producing more of the desired endonuclease. So both a small and a large colony was chosen from each plate on which different size colonies were found. These colonies were grown up at 37° C., induced with IPTG and collected 1.5 hours after induction. The broken cells were assayed for activity. The pAGR3-Rg1-1 DNA grown as a CsCl prep in the absence of any methylase genes had lost its HphI activity. The mini-prep pAGR3-Rg1-1 retained its activity as did the pAII3d-Rg1-1 DNA prepared by CsCl density gradient centrifugation or mini-preparation.

5B:

In another experiment, samples were taken at various times after IPTG-induction to see if that variable had a significant effect on the production of HphI restriction endonuclease. ER2497 cells containing pACYC184-CM6 and pCEF8-AM1 were transformed with pAII3d-Rg1-1 and selected on an antibiotic plate containing 100 μg/ml ampicillin, 50 μg/ml kanamycin and 30 μg/ml chloramphenicol. One large and one small colony from this plate were selected and cultured overnight at 30° C. with the above antibiotics. The overnight culture was used to inoculate a larger culture with the same antibiotics. Samples were taken at 1, 2, 4, 6 and 20 hours after IPTG-induction. The SNs and the broken cells were assayed for HphI endonuclease activity. No significant difference was seen between the activity in the broken cells or SNs originating from a large or a small colony; no difference was seen in enzyme activity in broken cells from samples taken at different time-points. However, an increasing level of enzyme activity was observed in the SNs as time post-induction increased.

5C:

The effect of rifampicin was tested on ER2497 cells containing pAII3d-Rg1-1, pACYC184-CM9-1 and pCEF8-AM1. Rifampicin is believed to inhibit bacterial RNA Polymerase, but not T7 RNA Polymerase, effectively turning off production of bacterial mRNAs and, in turn, bacterial proteins. This should free up the rest of the bacterial cell machinery for production of the T7 mRNAs and gene products. In addition, we hoped that rifampicin would prohibit the lambda lysogen in ER2497 cells from inducing lysis by inhibiting production of late lambda mRNAs and thus production of late lambda proteins required in the lytic cycle.

Cultures were inoculated from single colonies and grown overnight at 30° C. in Luria broth augmented with 100 μg/ml ampicillin, 30 μg/ml chloramphenicol and 50 μg/ml kanamycin. Overnight cultures were transferred to 200 ml of Luria broth containing the same antibiotics, and incubated with shaking at 30° C. prior to induction. At 25 min after IPTG-induction, the cultures were divided into two flasks; rifampicin was added to one flask to a final concentration of 200 μg/ml and the cultures were returned to the 30° C. shaker; samples were collected at 2 and 4 hours after IPTG-induction. The broken cells and SNs were tested for HphI endonuclease activity. Samples treated with rifampicin did not show increased HphI activity in the broken cells. However, there was less HphI endonuclease activity in the SNs from cells grown in the presence of rifampicin, indicating that less cell breakage was occurring during the induction period.

5D:

The effect of incubation temperature on HphI endonuclease activity was also tested. A single colony of ER2420 cells containing the methylase plasmids pSYX19-CM5-3 and pACYC184-AM6 and the endonuclease plasmid pAGR3-Rg1-1 was inoculated into 2 tubes of Luria broth containing 100 μg/ml ampicillin, 30 μg/ml chloramphenicol and 50 μg/ml kanamycin; one tube was incubated at 30° C. overnight, the other was incubated at 37° C. In the morning, the cultures were used to inoculate larger cultures containing 50 ml of fresh Luria broth augmented with the same antibiotics as above. The larger cultures were incubated at the same corresponding temperatures until they reached a Klett of 125, then were induced with IPTG for 4 hours. Endonuclease activity was measured in the SNs and broken cells. No activity was found in the SNs. No significant difference was seen between the activity in the broken cells grown at 30° C. or 37° C.

5E:

The four single methylase constructs were tested in ER2420 cells with the endonuclease cloned into pAGR3 to see if single methylases provided sufficient protection for HphI expression. Competent ER2420 cells containing pSYX19-CM5-3 or pACYC184-CM9-1 or pACYC184-AM6 or pSYX20-AM1 were transformed with pAGR3-Rg1-1 and selected on Luria agar plates spread with 100 μg/ml ampicillin and either 30 μg/ml chloramphenicol (pACYC184-CM9-1 or pACYC184-AM6) or 50 μg/ml kanamycin (pSYX19-CM5-3 or pSYX20-AM1). Single colonies were picked to inoculate overnight cultures in Luria broth plus the appropriate antibiotics, and grown at 30° C. These overnight cultures were used to inoculate 100 ml of fresh Luria broth plus antibiotics. The cultures were grown at 30° C. to a Klett of 125, and then were induced with IPTG to a final concentration of 0.4 mM. 50 ml samples were collected at 2 hours and 4 hours after induction. Little or no activity was seen in the SNs. The two constructs containing the endonuclease plasmid and (either) cytosine methylase construct also showed no activity in the broken cells at 2 hours post-induction, and only a hint of activity after 4 hours. It was apparent that these constructs had either lost the endonuclease plasmid or had mutated the gene to reduce its lethality. The broken cells containing the endonuclease plasmid and either adenine methylase plasmid did show activity, however, both at 2 and 4 hours after induction. The cells containing pACYC184-AM6 appeared to have more activity than those containing pSYX20-AM1, although the difference appeared to be minimal.

6. Conclusion

The best expression of HphI endonuclease activity came from either of the two endonuclease constructs coupled with at least the adenine methylase plasmid under the tetracycline promoter and containing a new *E. coli* ribosome binding site. The temperature at which the cells were incubated and the length of time the cells were allowed to grow after IPTG-induction didn't seem to influence the amount of HphI endonuclease activity. The use of the tac system reduced the loss of enzyme activity into the supernatant. The best activity we obtained was approximately 5,000 units/gram of cells, although it was a little difficult to gauge the titer accurately due, perhaps, to some contaminants in the reaction buffers which obscured the banding pattern somewhat.

A sample of *Escherichia coli* ER1398, pACYC184-HphRM6-7 has been deposited at the American Type Culture Collection on Jun. 27, 1995 and bears the ATCC Accession No. 69854.

What is claimed is:

1. Isolated DNA coding for HphI restriction endonuclease, wherein the isolated DNA is obtainable from the plasmid pACYC184-HphRM6-7.

2. A recombinant vector comprising a vector into which DNA coding for HphI restriction endonuclease has been inserted.

3. A recombinant vector comprising the isolated DNA of claim 1.

4. The recombinant vector of claim 3, wherein the vector comprises the plasmid pACYC184-HphRM6-7.

5. A host cell transformed with the recombinant vector of claim 2, 3 or 4.

6. A method of producing HphI restriction endonuclease comprising culturing a host cell transformed with the vector of claim 2, 3 or 4 under conditions suitable for expression of said endonuclease.

* * * * *

UNITED STATES PATENT AND TRADEMARK OFFICE
CERTIFICATE OF CORRECTION

PATENT NO. : 5,731,185  
DATED : March 24, 1998  
INVENTOR(S) : Meda, et al

Page 1 of 2

It is certified that error appears in the above-indentified patent and that said Letters Patent is hereby corrected as shown below:

Column 2, line 46, replace *Gene* 10:21 9-225 (1980) with --*Gene* 10:219-225 (1980)--

Column 7, line 44, replace "pHB" with --pH8--

Column 10, line 7, replace "labeted" with --labeled--

Column 10, line 27, replace "µg/ml:" with --µg/ml--

Column 11, line 2, replace "*coli* DNA" with --*coli*. DNA--

Column 11, line 21, replace "2" with --2 µl--

Column 11, line 29, replace "AATTTACT" with --AATTACT--

Column 11, line 34, replace "TTATGGG" with --TTATTGGG--

Column 12, line 51, replace "Example 1.14 transformants" with --Example 1.  14 transformants--

UNITED STATES PATENT AND TRADEMARK OFFICE
CERTIFICATE OF CORRECTION

PATENT NO. : 5,731,185  
DATED : March 24, 1998  
INVENTOR(S) : Meda, et al

It is certified that error appears in the above-indentified patent and that said Letters Patent is hereby corrected as shown below:

Column 13, line 46, replace "the 5 disclosure" --the disclosure--.

Signed and Sealed this

Twenty-first Day of July, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 75 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

```
ATGCARATHT AYGARACNTA YTGGGARATH ACNAAYGART AYGGNTAYAA YACNGCNCGN    60
TTYGTNGARA CNAGR                                                    75
```

( 2 ) INFORMATION FOR SEQ ID NO:2:

( i ) SEQUENCE CHARACTERISTICS:
        ( A ) LENGTH: 24 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:2:

```
Met Gln Ile Tyr Glu Thr Tyr Trp Glu Ile Thr Asn Glu Tyr Gly Tyr
1               5                   10                  15
Asn Thr Ala Arg Phe Val Glu Thr
            20
```

( 2 ) INFORMATION FOR SEQ ID NO:3:

( i ) SEQUENCE CHARACTERISTICS:
        ( A ) LENGTH: 76 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

```
GCACTAAGCT TATGCATGCA TTAACTTTAA GGAGGATATA ACCATGGAAA TTTATGAAAC    60
TTATTGGGAA ATTACT                                                   76
```

( 2 ) INFORMATION FOR SEQ ID NO:4:

( i ) SEQUENCE CHARACTERISTICS:
        ( A ) LENGTH: 76 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

```
GCACTAAGCT TATGCATGCA TTAACTTTAA GGAGGATATA ACCATGCAAA TTTATGAAAC    60
TTATTGGGAA ATTACT                                                   76
```

( 2 ) INFORMATION FOR SEQ ID NO:5:

( i ) SEQUENCE CHARACTERISTICS:
   ( A ) LENGTH: 28 base pairs
   ( B ) TYPE: nucleic acid
   ( C ) STRANDEDNESS: unknown
   ( D ) TOPOLOGY: unknown ( i i ) MOLECULE TYPE: DNA (genomic)

( x i ) SEQUENCE DESCRIPTION: SEQ ID NO:5:

CTGCGAGATC TAGCTTGCAT GCCTGCAG                                                             28

( 2 ) INFORMATION FOR SEQ ID NO:6:

( i ) SEQUENCE CHARACTERISTICS:
      ( A ) LENGTH: 250 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:6:

GAATTGTGAG CGCTCACAAT TCTAGGATGT TAATTGCGCC GACATCATAA CGGTTCTGGC           60

AAATATTCTG AAATGAGCTG TTGACAATTA ATCATCGGCT CGTATAATGT GTGGAATTGT          120

GAGCGGATAA CAATTTCACA CAGGAAACAG ACCATGGTGA ATTCTAGAGC TCGAGGATCC          180

GCGGTACCCG GGCATGCATT CGAAGCTTCC TTAAGCGGCC GTCGACCGAT GCCCTTGAGG          240

CCTTCAACCA                                                                 250

( 2 ) INFORMATION FOR SEQ ID NO:7:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:7:

AGCTCAAGCA ATTGCCGAAG CAGTGTTAAA AAGGAA                                    36

( 2 ) INFORMATION FOR SEQ ID NO:8:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:8:

ACGCTCTGTG TTGGATCCGT ATTCA                                                25